(12) United States Patent
Till et al.

(10) Patent No.: US 7,814,940 B2
(45) Date of Patent: Oct. 19, 2010

(54) BEVERAGE FILLING PLANT FOR FILLING BEVERAGE BOTTLES OR CONTAINERS WITH A LIQUID BEVERAGE FILLING MATERIAL HAVING A BEVERAGE BOTTLE OR CONTAINER TREATMENT ARRANGEMENT AND A METHOD OF OPERATION THEREOF

(75) Inventors: Volker Till, Hofheim/Taunus (DE); Daryoush Sangi, Hamburg (DE)

(73) Assignee: KHS Maschinen- und Anlagenbau AG, Dortmund (DE)

( * ) Notice: Subject to any disclaimer, the term of this patent is extended or adjusted under 35 U.S.C. 154(b) by 883 days.

(21) Appl. No.: 11/677,213

(22) Filed: Feb. 21, 2007

(65) Prior Publication Data

US 2008/0023097 A1    Jan. 31, 2008

(30) Foreign Application Priority Data

Feb. 21, 2006    (DE) .................... 10 2006 007 944

(51) Int. Cl.
*B65B 3/04* (2006.01)

(52) U.S. Cl. .................... 141/11; 141/5; 141/92; 141/144

(58) Field of Classification Search .................. 141/5, 141/11, 92, 144
See application file for complete search history.

(56) References Cited

U.S. PATENT DOCUMENTS

| | | | |
|---|---|---|---|
| 4,296,068 A | * | 10/1981 | Hoshino ............ 422/62 |
| 6,120,730 A | * | 9/2000 | Palaniappan et al. ...... 422/28 |
| 6,544,473 B1 | * | 4/2003 | Shintaku et al. ............ 422/26 |
| 7,497,237 B2 | * | 3/2009 | Till ........................ 141/5 |
| 2004/0237466 A1 | * | 12/2004 | Grossmann et al. ........ 53/167 |
| 2005/0161110 A1 | * | 7/2005 | Topf ....................... 141/85 |

FOREIGN PATENT DOCUMENTS

| | | |
|---|---|---|
| DE | 11 91 676 | 4/1965 |
| DE | 30 47 087 A1 | 7/1982 |
| DE | 90 12 065 U1 | 3/1991 |
| DE | 199 49 692 A1 | 4/2001 |
| EP | 0 381 841 | 8/1990 |
| EP | 1 086 896 | 3/2001 |
| WO | WO 00/00394 | 1/2000 |
| WO | WO 01/78791 | 10/2001 |
| WO | WO 03/070024 | 8/2003 |

OTHER PUBLICATIONS

European Search Report EP 07 00 3481 and English translation thereof.

* cited by examiner

*Primary Examiner*—Gregory L Huson
*Assistant Examiner*—Nicolas A Arnett
(74) *Attorney, Agent, or Firm*—Nils H. Ljungman & Associates (57) ABSTRACT

A beverage filling plant for filling beverage bottles or containers with a liquid beverage filling material having a beverage bottle or container treatment arrangement and a method of operation thereof. The container treatment arrangement has a nozzle structure designed to dispense treatment medium, such as an aerosol mixture of air and hydrogen peroxide, into additional sections of a container, such as a hollow handle or hollow projections on the mouth of the container, to sterilize the interior surfaces thereof.

19 Claims, 5 Drawing Sheets

BEVERAGE FILLING PLANT FOR FILLING BEVERAGE BOTTLES OR CONTAINERS WITH A LIQUID BEVERAGE FILLING MATERIAL HAVING A BEVERAGE BOTTLE OR CONTAINER TREATMENT ARRANGEMENT AND A METHOD OF OPERATION THEREOF

BACKGROUND

This application relates to a beverage filling plant for filling beverage bottles or containers with a liquid beverage filling material having a beverage bottle or container treatment arrangement and a method of operation thereof.

A beverage bottling plant for filling bottles with a liquid beverage filling material can possibly comprise a beverage filling machine, which is often a rotary filling machine, with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material.

Some beverage bottling plants may possibly comprise filling arrangements that receive a liquid beverage material from a toroidal or annular vessel, in which a supply of liquid beverage material is stored under pressure by a gas. The toroidal vessel may also be connected to at least one external reservoir or supply of liquid beverage material by a conduit or supply line. In some circumstances it may even be possible that a beverage bottling plant has two external supply reservoirs, each of which may be configured to store either the same liquid beverage product or different products. These reservoirs could possibly be connected to the toroidal or annular vessel by corresponding supply lines, conduits, or other arrangements. It is also possible that the external supply reservoirs could be in the form of simple storage tanks, or in the form of liquid beverage product mixers.

A wide variety of types of filling elements are used in filling machines in beverage bottling or container filling plants for dispensing a liquid product into bottles, cans or similar containers, including but not limited to filling processes that are carried out under counterpressure for the bottling of carbonated beverages. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine.

After a filling process has been completed, the filled beverage bottles are transported or conveyed to a closing machine, which is often a rotary closing machine. A revolving or rotary machine comprises a rotor, which revolves around a central, vertical machine axis. There may further be provided a conveyer arrangement configured to transfer filled bottles from the filling machine to the closing station. A transporting or conveying arrangement can utilize transport star wheels as well as linear conveyors. A closing machine closes bottles by applying a closure, such as a screw-top cap or a bottle cork, to a corresponding bottle mouth. Closed bottles are then usually conveyed to an information adding arrangement, wherein information, such as a product name or a manufacturer's information or logo, is applied to a bottle. A closing station and information adding arrangement may be connected by a corresponding conveyer arrangement. Bottles are then sorted and packaged for shipment out of the plant.

Many beverage bottling plants may also possibly comprise a rinsing arrangement or rinsing station to which new, non-return and/or even return bottles are fed, prior to being filled, by a conveyer arrangement, which can be a linear conveyor or a combination of a linear conveyor and a starwheel. Downstream of the rinsing arrangement or rinsing station, in the direction of travel, rinsed bottles are then transported to the beverage filling machine by a second conveyer arrangement that is formed, for example, by one or more starwheels that introduce bottles into the beverage filling machine.

It is a further possibility that a beverage bottling plant for filling bottles with a liquid beverage filling material can be controlled by a central control arrangement, which could be, for example, a computerized control system that monitors and controls the operation of the various stations and mechanisms of the beverage bottling plant.

This invention relates to a method as described in the introduction of Claim 1 and to an apparatus for the performance of the method as described in the introduction to Claim 7.

The sterilization of bottles or similar containers by the application of hydrogen peroxide ($H_2O_2$) to the interior surfaces of the container to be sterilized, e.g. with the use of a treatment medium in the form of an aerosol consisting of sterile air and the hydrogen peroxide and the subsequent treatment of the interior surfaces of the container with hot sterile air to heat the respective container and to activate the sterilization and to remove this medium as well as any quantities of residual water at the end of the sterilization phase or sterilization process is described in the prior art.

The treatment media are introduced by means of a treatment nozzle which has a single nozzle opening that is directed toward the bottom of the respective container, so that the respective treatment medium, among other things, after it strikes the container bottom, flows upward on the interior surface of the container and is thereby uniformly distributed on the interior surfaces of the container.

The effectiveness of the sterilization process depends on an optimized flow of the respective treatment medium, i.e. the treatment medium must be made to flow so that all the areas of the interior surface of the container are covered by the treatment medium or are contacted by this medium.

If bottles or similar containers have an internal contour that is different from the conventional continuous shape, in particular if wider areas or partially enclosed interior areas where flow conditions are less than ideal are formed by the internal contour of the container, an effective sterilization is not possible using the methods of the prior art and the media these methods of the prior art employ.

The object of the invention is to describe a method that makes it possible to also sterilize in an optimal manner bottles or similar containers with an internal contour that differs from the conventional shape and forms expanded areas and/or additional enclosed interior portions etc. The invention teaches a method described in Claim 1. The object of Claim 7 is an apparatus.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

At least one possible embodiment of the present application is explained in greater detail below illustrated in the accompanying drawings, in which.

DESCRIPTION OF EMBODIMENT OR EMBODIMENTS

Figure 1:
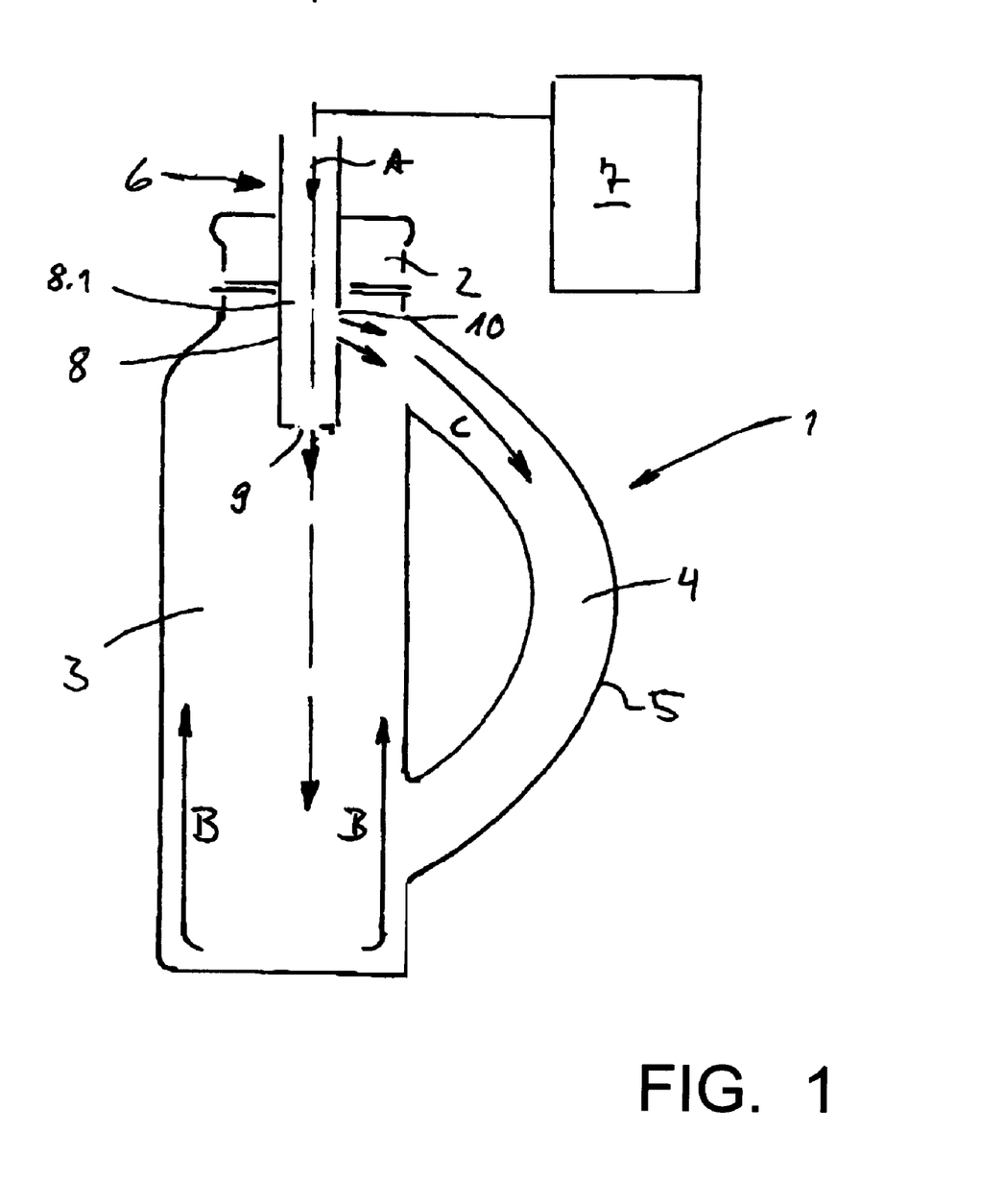
FIG. 1 is a simplified schematic illustration of a bottle with a shape that is different from the conventional bottle shape, together with a treatment nozzle that is introduced into the bottle for the introduction of a treatment medium into the interior of the bottle during the bottle sterilization.
Figure 1A:
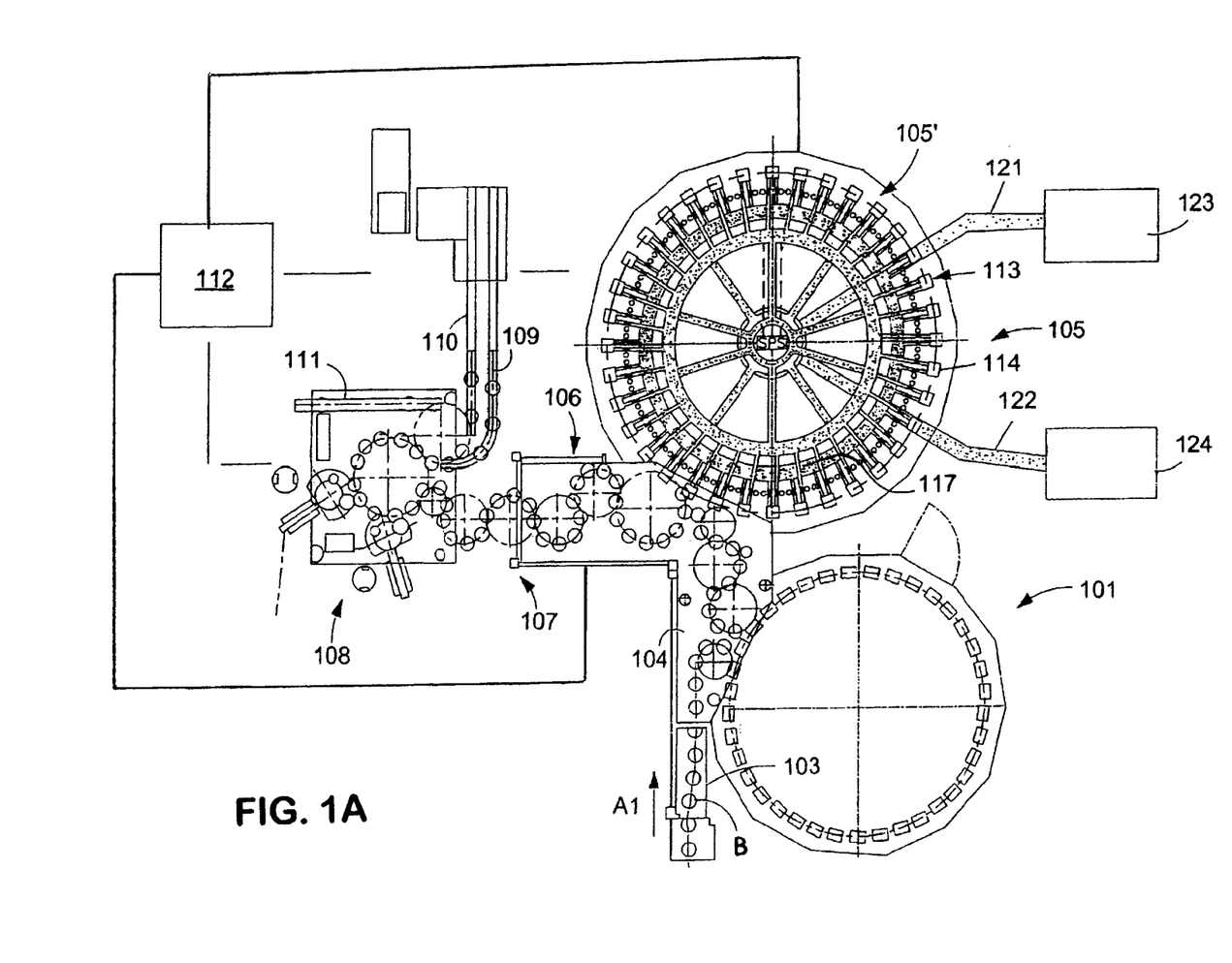
FIG. 1A shows schematically the main components of one possible embodiment example of a system for filling containers.

FIG. 1A shows schematically the main components of one possible embodiment example of a system for filling containers, specifically, a beverage bottling plant for filling bottles B with at least one liquid beverage, in accordance with at least one possible embodiment, in which system or plant could possibly be utilized at least one aspect, or several aspects, of the embodiments disclosed herein.

FIG. 1A shows a rinsing arrangement or rinsing station 101, to which the containers, namely bottles B, are fed in the direction of travel as indicated by the arrow A1, by a first conveyer arrangement 103, which can be a linear conveyor or a combination of a linear conveyor and a starwheel. Downstream of the rinsing arrangement or rinsing station 101, in the direction of travel as indicated by the arrow A1, the rinsed bottles B are transported to a beverage filling machine 105 by a second conveyer arrangement 104 that is formed, for example, by one or more starwheels that introduce bottles B into the beverage filling machine 105.

The beverage filling machine 105 shown is of a revolving or rotary design, with a rotor 105', which revolves around a central, vertical machine axis. The rotor 105' is designed to receive and hold the bottles B for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles B to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 1A, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle B, the first product or the second product can be filled by means of an appropriate control of the filling product or fluid valves.

Downstream of the beverage filling machine 105, in the direction of travel of the bottles B, there can be a beverage bottle closing arrangement or closing station 106 which closes or caps the bottles B. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles B. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles B to different locations.

The first output conveyer arrangement 109, in the embodiment shown, is designed to convey bottles B that are filled with a first type of liquid beverage supplied by, for example, the supply reservoir 123. The second output conveyer arrangement 110, in the embodiment shown, is designed to convey bottles B that are filled with a second type of liquid beverage supplied by, for example, the supply reservoir 124. The third output conveyer arrangement 111, in the embodiment shown, is designed to convey incorrectly labeled bottles B. To further explain, the labeling arrangement 108 can comprise at least one beverage bottle inspection or monitoring device that inspects or monitors the location of labels on the bottles B to determine if the labels have been correctly placed or aligned on the bottles B. The third output conveyer arrangement 111 removes any bottles B which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

In FIG. 1, 1 is a bottle or a bottle-like container with a special shape, and specifically one in which the interior or the volume of the bottle 2 is formed not only by the bottle space 3 that is adjacent axially to the bottle mouth 2, but also by a partial or secondary space, namely by the interior 4 of a hollow handle 5 which is molded onto the bottle 1.

To guarantee, during the sterilization process, sufficient treatment not only of the bottle space 3, but also of the partial or secondary space 4 with the treatment media (first with an aerosol consisting of sterile air and hydrogen peroxide and then with hot sterile air), for the introduction of the sterilization or treatment media a treatment nozzle 6 is used which is part of a treatment or sterilization apparatus that is schematically illustrated by block 7 in FIG. 1 and which, with its tube-like nozzle body, is introduced through the bottle mouth 2 into the bottle 1, and specifically, for example, so that the axis of the nozzle body 8 is coaxial with the bottle axis FA.

The treatment and sterilization device 7 then has, for example—apart from the special realization of the treatment nozzle 6—the structure of such a device that will be familiar to a technician skilled in the art.

The treatment media are fed to the nozzle body 8 and/or to the nozzle conduit 8.1 realized in this body, as indicated by the arrow A. On the free end, the nozzle body 8 forms at least one nozzle opening 9 for the discharge of the treatment media, in particular for the treatment of the bottle space 3 and the interior surfaces of the bottle 1 that define this space. To also ensure an effective treatment of the partial space 4 with the treatment media, the nozzle body 8 has, on its peripheral surface, additional nozzle openings 10 that are also in communication with the nozzle conduit 8.1, from which a portion of the treatment media fed to the nozzle conduit 8.1 is discharged in a direction that is radial or approximately radial to the axis of the nozzle body 8, and thereby gets into the partial space 4 formed by the handle 5, so that this latter area can also be reliably sterilized.

Figures 2, 3:
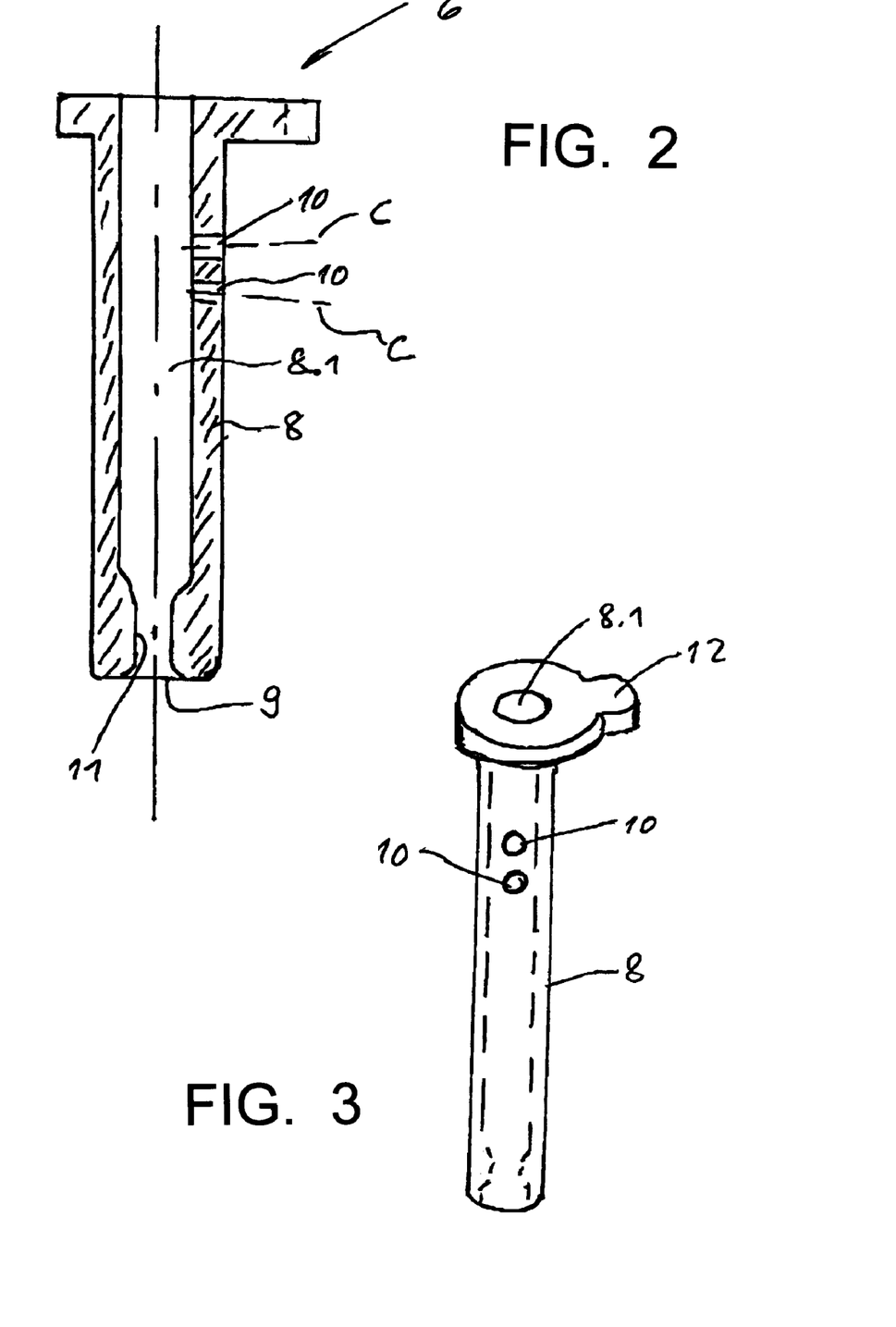
FIG. 2 shows a partial section through the nozzle shown in FIG. 1.
FIG. 3 is a perspective view showing the treatment nozzle shown in FIG. 1.

To ensure that a sufficient amount of treatment medium is discharged through the nozzle openings 10, the nozzle conduit 8.1, downstream of the nozzle apertures 10, has a constriction as indicated at 11 in FIG. 2.

In addition, during the sterilization process, the bottle 1 and the nozzle 6 are oriented relative to each other so that the nozzle openings 10 and their axis are oriented toward that area of the internal surface of the bottle 1 in which the partial space 4 emerges with its upper end, i.e. the end closer to the bottle mouth 2, into the bottle space 3. To guarantee this orientation, the bottles 1 are placed in a predetermined orientation by means of a transport system (not shown) for the sterilization process. The nozzle 6 is also realized, for example by a special shape of its nozzle body 8, so that it can only be fastened on a nozzle carrier of the apparatus 7 used for the sterilization process in the orientation required for the treatment of the bottles 1. As shown in FIG. 3, for this purpose, the nozzle body 8 has an orientation guide in the form of a bracket 12 that projects radially on its upper end.

During the sterilization process, the nozzle aperture 9 is oriented with its axis toward the bottom of the bottle 1 or of the interior space of the bottle, so that the treatment medium that is discharged from this nozzle aperture strikes the bottom and is then at least partly optimally distributed upward on the interior surfaces of the bottle space 3, as illustrated by arrow B in FIG. 1. The treatment medium that is discharged from the additional nozzle aperture gets into the partial space 4, as illustrated by arrow C in FIG. 1, so that the overall result is an optimal flow that guarantees uniform contact between all areas of the internal surface of the bottle and the respective treatment medium.

Figure 4:
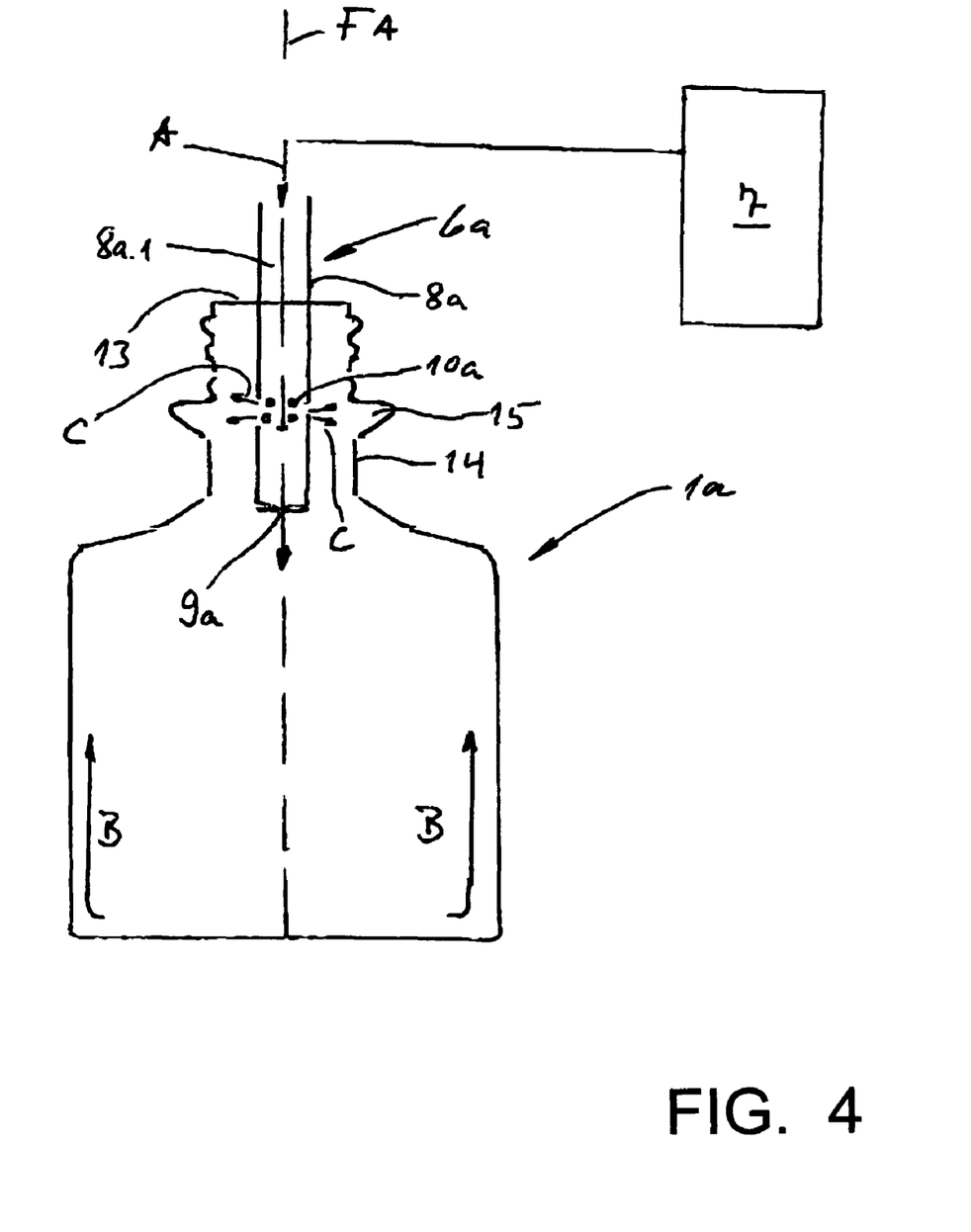
FIG. 4 shows an additional possible embodiment in a view like FIG. 1.
Figure 5:
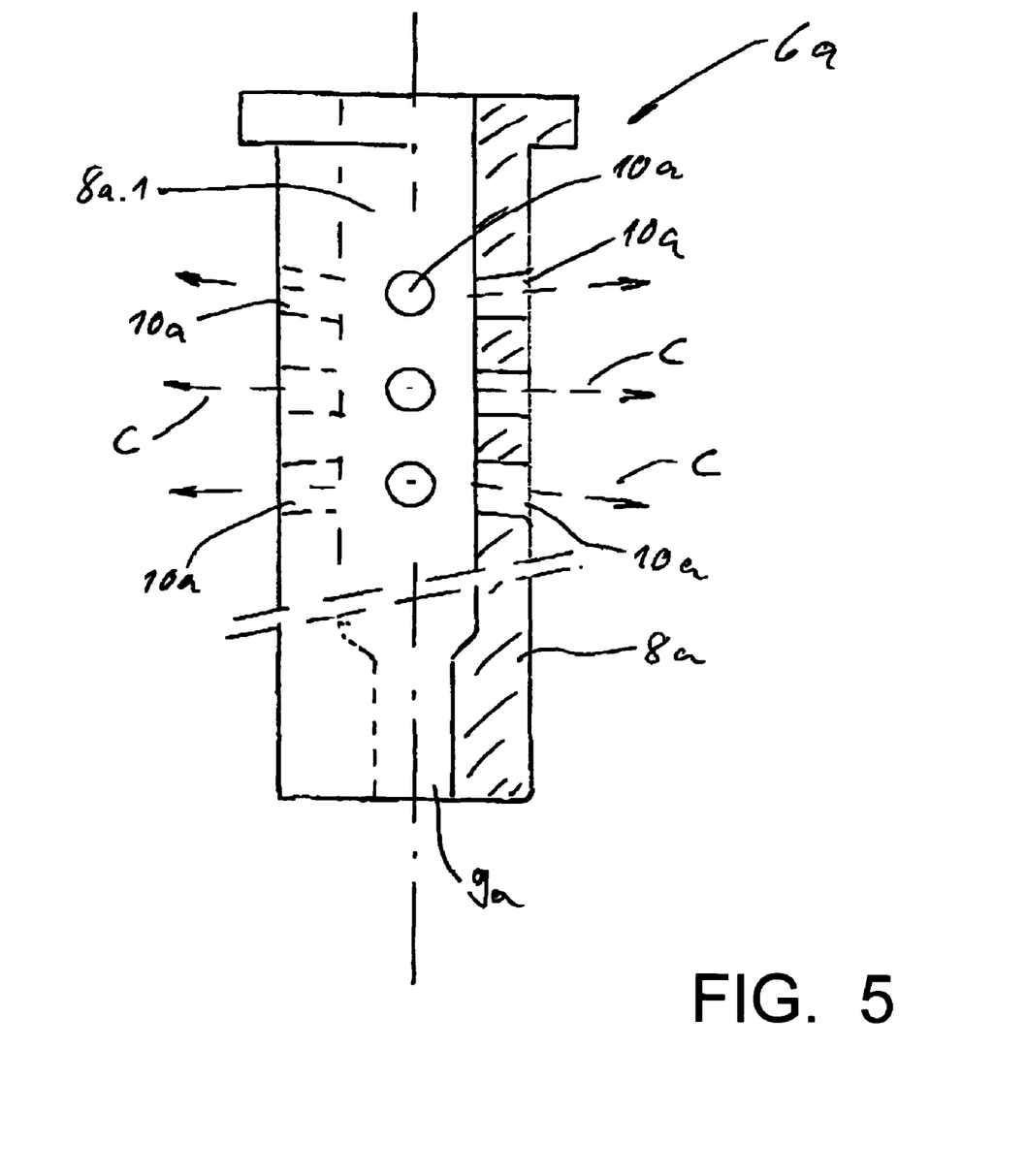
FIG. 5 shows a section through the treatment nozzle shown in FIG. 4.

FIG. 4 shows, in an illustration that is similar to FIG. 1, a bottle 1*a* in the interior of which, in the vicinity of its bottle neck 14 which is adjacent to the bottle mouth 13, there is, among other things an expanded section that forms a secondary or partly enclosed interior space 15. To also treat this secondary or partly enclosed space 15 which surrounds the bottle axis FA in a ring shape with sufficient sterilization medium, the nozzle 6*a* that corresponds to the nozzle 6 has a plurality of additional nozzle apertures 10*a* on the peripheral or envelope surface of its tubular nozzle body 8*a*. In the exemplary embodiment illustrated here, these additional nozzle apertures are provided in a plurality of groups that each surround the axis of the nozzle body 8 in a ring shape and are axially offset in the axial direction of the nozzle body 8*a*, and specifically so that each group has a plurality of nozzle apertures 10*a*, which are then distributed, for example, at equal angular intervals around the axis of the nozzle body 8*a*. The nozzle openings 10*a* of the individual groups are oriented, for example, with their axis in a different axial orientation, as illustrated in FIG. 5, so that not only the areas immediately opposite this secondary space 15, with its nozzle apertures 10*a*, but also other areas of the internal surface of the bottle neck 14 that are realized with a profiling or a varying contour are optimally contacted by the treatment media. The nozzle apertures 10*a* can be realized, for example, with a round or oval cross section or in the form of slots.

In this exemplary embodiment, to guarantee that a sufficient quantity of the respective treatment medium is discharged from the nozzle apertures 10*a*, the nozzle conduit 8*a*.1 that is realized in the nozzle body 8*a* is in turn constricted in the flow direction toward the nozzle apertures 10*a*, and/or the nozzle opening 9*a* corresponding to the nozzle aperture 9 on the lower end of the nozzle body 8*a* has a cross section that is reduced with respect to the cross section of the nozzle conduit 8*a*.1, as illustrated in FIG. 5.

The invention was explained above on the basis of exemplary embodiments. It goes without saying that modifications and variants are possible without thereby going beyond the basic teaching of the invention.

One feature that all of the embodiments of the invention have in common is that during the sterilization process, the respective treatment medium is introduced via additional nozzle apertures into the expanded areas and/or secondary areas of the interior of the container or bottle formed by the shape of the container, i.e. the interior surfaces of these portions of the container are also contacted by the respective treatment medium, and the containers or bottles are therefore treated with treatment nozzles which, in terms of their arrangement and number of nozzle openings, are adapted to the internal contour of the containers or bottles and thus ensure an optimal contact of all areas of the interior surface of a container or of a bottle with the respective treatment medium and an optimal flow of the treatment medium during the sterilization process.

For purposes of simplification, it has been assumed in the above description that the nozzle apertures are formed by discharge apertures. Basically, it is also possible to use special nozzle elements, each of which then forms one or possibly more nozzle discharge apertures, and specifically, for example, with a special nozzle or flow characteristic.

AT LEAST PARTIAL NOMENCLATURE: 1, 1*a* Bottle; 2 Bottle mouth; 3 Bottle interior; 4 Partial space; 5 Handle; 6, 6*a* Treatment nozzle; 7 Apparatus; 8, 8*a* Nozzle body; 8.1, 8*a*.1 Nozzle conduit; 9, 9*a* Nozzle aperture; 10, 10*a* Nozzle aperture; 11 Constriction; 12 Orientation aid or strap; 13 Bottle mouth; 14 Bottle neck; 15 Secondary space; A Flow direction of the introduced treatment medium; B, C Flow direction of the treatment medium inside the bottle.

One feature or aspect of an embodiment is believed at the time of the filing of this patent application to possibly reside broadly in a method of operating a beverage filling plant for filling beverage bottles or beverage containers with liquid beverage material, said beverage bottling plant comprising: a beverage bottle or container filling machine being configured and disposed to fill beverage bottles or containers with liquid beverage material; said beverage bottle or container filling machine comprising: a rotor; a rotatable vertical machine column; said rotor being connected to said vertical machine column to permit rotation of said rotor about said vertical machine column; a plurality of beverage bottle or container filling elements for filling beverage bottles or containers with liquid beverage material being disposed on the periphery of said rotor; each of said plurality of beverage bottle or container filling elements comprising a container carrier being configured and disposed to receive and hold beverage bottles or containers to be filled; each of said plurality of beverage bottle or container filling elements being configured and disposed to dispense liquid beverage material into beverage bottles or containers to be filled; at least one liquid reservoir being configured to hold a supply of liquid beverage material; at least one supply line being configured and disposed to connect said at least one liquid reservoir to said beverage bottle or container filling machine to supply liquid beverage material to said beverage bottle or container filling machine; a first star wheel structure being configured and disposed to move beverage bottles or containers into said beverage bottle or container filling machine; and a second star wheel structure being configured and disposed to move beverage bottles or containers out of said beverage bottle or container filling machine; a beverage bottle or container closing machine being configured and disposed to close tops of filled beverage bottles or containers; said beverage bottle or container closing machine comprising: a rotor; a rotatable vertical machine column; said rotor being connected to said vertical machine column to permit rotation of said rotor about said vertical machine column; a plurality of closing devices being disposed on the periphery of said rotor; each of said plurality of closing devices being configured and disposed to place closures on filled beverage bottles or containers; each of said plurality of closing devices comprising a container carrier being configured and disposed to receive and hold filled beverage bottles or containers; a first star wheel structure being configured and disposed to move filled beverage bottles or containers into said beverage bottle or container closing machine; and a second star wheel structure being configured and disposed to move filled, closed beverage bottles or containers out of said beverage bottle or container closing machine; a beverage bottle or container treatment machine being configured and disposed to treat empty beverage bottles or containers prior to filling; said beverage bottle or container treatment machine comprising: at least one jet structure being configured to dispense treatment medium into beverage bottles or containers to treat the interiors thereof; said at least one jet structure comprises a plurality of openings out of which treatment medium is sprayed; said plurality of openings being positioned to conform to the inner contour of the beverage bottles or containers to be treated; at least one of said openings being configured and disposed to spray treatment medium into a main interior portion of the beverage bottles or containers during treatment of the beverage bottles or containers; at least one other of said openings being configured and disposed to spray treatment medium into an additional enclosed interior portion of the beverage bottles or containers adjacent a main interior portion of the beverage bottles or containers, which additional enclosed interior portion comprises a projection, an enlargement, a handle, or other structure during treatment of the beverage bottles or containers; a first conveyor arrangement being configured and disposed to convey beverage bottles or containers to be treated to said beverage bottle or container treatment machine; a second conveyor arrangement being configured and disposed to convey treated beverage bottles or containers from said beverage bottle or container treatment machine to said beverage bottle or container filling machine; a third conveyor arrangement being configured and disposed to convey filled beverage bottles or containers from said beverage bottle or container filling machine to said beverage bottle or container closing machine; said method comprising the steps of: moving beverage bottles or containers to said beverage bottle or container treatment machine; treating beverage bottles or containers in said beverage bottle or container treatment machine; said step of treating comprising: introducing said jet structure into a corresponding beverage bottle or container; treating a main interior portion of the beverage bottle or container by dispensing treatment medium through at least one of said openings; and treating an additional interior portion of the beverage bottle or container by dispensing treatment medium through at least one other of said openings; moving beverage bottles or containers from said beverage bottle or container treatment machine to said beverage bottle or container filling machine; filling beverage bottles or containers in said beverage bottle or container filling machine; moving beverage bottles or containers from said beverage bottle or container filling machine to said beverage bottle or container closing machine; and closing beverage bottles or containers in said beverage bottle or container closing machine.

One feature or aspect of an embodiment is believed at the time of the filing of this patent application to possibly reside broadly in a method for the sterilization or bottles or similar containers (1, 1*a*) with the use of at least one sterilization or treatment medium which is applied to the internal surface of the container via at least one treatment nozzle (6, 6*a*) which is introduced into the respective container (1, 1*a*), whereby the treatment nozzle (6, 6*a*) has a plurality of nozzle apertures (9, 9*a*; 10, 10*a*), the number and/or arrangement of which are adapted to the internal contour of the respective container, characterized in that for the treatment of containers with an internal contour that forms expanded areas and/or secondary areas (4, 15), the treatment nozzle (6, 6*a*) is introduced into the respective container (1, 1*a*) so that at least one nozzle aperture (10, 10*a*) is directed with its axis of action toward the expanded portion and/or the secondary area (4, 15) of the internal contour.

Another feature or aspect of an embodiment is believed at the time of the filing of this patent application to possibly reside broadly in the method, characterized by the use of at least one treatment nozzle with at least one first nozzle aperture (9, 9*a*) directed toward the container bottom and with at least one additional nozzle aperture (10, 10*a*) directed toward the expanded portion and/or the secondary area (4, 15).

Yet another feature or aspect of an embodiment is believed at the time of the filing of this patent application to possibly reside broadly in the method, characterized in that the treatment medium is discharged from the at least one additional nozzle aperture (10, 10*a*) radially or approximately radially with respect to a container axis (FA).

Still another feature or aspect of an embodiment is believed at the time of the filing of this patent application to possibly reside broadly in the method, characterized in that.

A further feature or aspect of an embodiment is believed at the time of the filing of this patent application to possibly reside broadly in the method, characterized in that the at least one treatment medium is discharged from the at least one additional nozzle aperture (10, 10*a*) at an angle with respect to the container axis (FA).

Another feature or aspect of an embodiment is believed at the time of the filing of this patent application to possibly reside broadly in the method, characterized in that the at least one treatment medium contains hydrogen peroxide, for example an aerosol consisting of sterile air and hydrogen peroxide.

One feature or aspect of an embodiment is believed at the time of the filing of this patent application to possibly reside broadly in an apparatus or the sterilization of bottles or similar containers, with at least one treatment nozzle (6, 6a) which is introduced during the sterilization process into the respective container (1, 1a) for the application of a sterilization or treatment medium to the interior surfaces of the container, whereby the treatment nozzle (6, 6a) has a plurality of nozzle openings (9, 9a; 10, 10a), the number and/or arrangement of which is/are adapted to the internal contour of the respective container, characterized in that for the treatment of containers (1, 1a) with an internal contour that forms at least one expanded area and/or at least one secondary or partly enclosed area (4, 15), the nozzle body is introduced into the respective container (1, 1a) during the treatment so that the at least one nozzle opening (10, 10a) is oriented with its working axis facing the at least one expanded area or the at least one secondary or partly enclosed area (4, 15).

Another feature or aspect of an embodiment is believed at the time of the filing of this patent application to possibly reside broadly in the apparatus, characterized in that the treatment nozzle (6, 6a) has on its nozzle body (8, 8a), at least two nozzle openings (9, 9a) which are oriented in different directions with their working axes.

Yet another feature or aspect of an embodiment is believed at the time of the filing of this patent application to possibly reside broadly in the apparatus, characterized in that the treatment nozzle (6, 6a) has at least one nozzle opening which, during the sterilization process, is directed with its working axis toward the bottom of the respective container.

Still another feature or aspect of an embodiment is believed at the time of the filing of this patent application to possibly reside broadly in the apparatus, characterized in that the treatment nozzle (6, 6a), on a tubular or rod-shaped nozzle body (8, 8a) that can be introduced into the respective container (1, 1a) has at least a first nozzle opening (9, 9a) directed toward the bottom of the container (1, 1a) and on the periphery of the nozzle body (8, 8a) at least one additional nozzle opening (10, 10a).

A further feature or aspect of an embodiment is believed at the time of the filing of this patent application to possibly reside broadly in the apparatus, characterized in that when the treatment nozzle (6, 6a) is introduced into the respective container (1, 1a), at least one nozzle opening (10, 10a) is opposite the at least one expanded portion and/or the at least one secondary or partly enclosed area (4, 15), for example located radially or approximately radially opposite in relation to a container axis (FA).

Another feature or aspect of an embodiment is believed at the time of the filing of this patent application to possibly reside broadly in the apparatus, characterized in that on the periphery of the nozzle body (8) there are a plurality of nozzle openings (10, 10a), which are all oriented differently with their working axes.

The invention relates to a method for the sterilization of bottles or similar containers using at least one treatment medium which is applied to the interior surface of the container via at least one treatment nozzle which is introduced into the container through a container opening.

Some examples of bottling and container handling systems and components thereof which may possibly be utilized or adapted for use in at least one possible embodiment, may possibly be found in the following U.S. Pat. No. 6,484,477, entitled "Capping Machine for Capping and Closing Containers, and a Method for Closing Containers;" U.S. Pat. No. 6,474,368, entitled "Beverage Container Filling Machine, and Method for Filling Containers with a Liquid Filling Material in a Beverage Container Filling Machine;" U.S. Pat. No. 6,494,238, entitled "A Plant for Filling Beverage into Beverage Bottles Other Beverage Containers Having Apparatus for Replacing Remaining Air Volume in Filled Beverage Bottles or Other Beverage Containers;" U.S. Pat. No. 6,470,922, entitled "Apparatus for the Recovery of an Inert Gas;" U.S. Pat. No. 6,463,964, entitled "Method of Operating a Plant for Filling Bottles, Cans or the like Beverage Containers with a Beverage, and a Beverage Container Filling Machine;" U.S. Pat. No. 6,834,473, entitled "Bottling Plant and Method of Operating a Bottling Plant and a Bottling Plant with Sections for Stabilizing the Bottled Product;" U.S. Pat. No. 6,484,762, entitled "A Filling System with Post-dripping Prevention;" U.S. Pat. No. 6,668,877, entitled "Filling System for Still Beverages;" U.S. Pat. No. 7,024,841, entitled "Labeling Machine with a Sleeve Mechanism for Preparing and Applying Cylindrical Labels onto Beverage Bottles and Other Beverage Containers in a Beverage Container Filling Plant;" U.S. Pat. No. 6,971,219 entitled "Beverage Bottling Plant for Filling Bottles with a Liquid Beverage Filling Material and a Labeling Station for Labeling Filled Bottles and Other Containers;" U.S. Pat. No. 6,973,767, entitled "Beverage bottling plant and a conveyor arrangement for transporting packages;" U.S. Pat. No. 7,013,624, entitled "Beverage bottling plant for filling bottles with a liquid beverage filling material, a container filling plant container information adding station, such as, a labeling station, configured to add information to containers, such as, bottles and cans, and modules for labeling stations;" No. U.S. Pat. No. 7,108,025, entitled "Beverage Bottling Plant for Filling Bottles with a Liquid Beverage Filling Material, and a Container Filling Lifting Device for Pressing Containers to Container Filling Machines;" U.S. Pat. No. 7,062,894, entitled "Beverage Bottling Plant for Filling Bottles with a Liquid Beverage Filling Material, and a Container Filling Plant Container Information Adding Station, Such As, a Labeling Station Having a Sleeve Label Cutting Arrangement, Configured to Add Information to Containers, Such As, Bottles and Cans;" U.S. Pat. No. 7,010,900, entitled "Beverage Bottling Plant for Filling Bottles with a Liquid Beverage Filling Material, and a Cleaning Device for Cleaning Bottles in a Beverage Bottling Plant;" U.S. Pat. No. 6,918,417, entitled "A Beverage Bottling Plant for Filling Bottles with a Liquid Beverage Filling Material, and an Easily Cleaned Lifting Device in a Beverage Bottling Plant;" U.S. Pat. No. 7,065,938, entitled "A Beverage Bottling Plant for Filling Bottles with a Liquid Beverage Filling Material, and a Container Filling Plant Container Information Adding Station, Such As, a Labeling Station Having a Gripper Arrangement, Configured to Add Information to Containers, Such As, Bottles and Cans;" U.S. Pat. No. 6,901,720, entitled "A Beverage Bottling Plant for Filling Bottles with a Liquid Beverage Filling Material, and Apparatus for Attaching Carrying Grips to Containers with Filled Bottles;" and U.S. Pat. No. 7,121,062 "Beverage bottling plant for filling bottles with a liquid beverage filling material, having a container handling machine with interchangeable receptacles for the container mouth."

The components disclosed in the various publications, disclosed or incorporated by reference herein, may possibly be used in possible embodiments of the present invention, as well as equivalents thereof.

Some examples of bottling and container handling systems and components thereof which may possibly be utilized or adapted for use in at least one possible embodiment, may possibly be found in the following U.S. patent applications Ser. No. 10/723,451, filed on Nov. 26, 2003, entitled "Beverage Bottling Plant for Filling Beverage Bottles or Other Beverage Containers with a Liquid Beverage Filling Material and Arrangement for Dividing and Separating of a Stream of Beverage Bottles or Other Beverage Containers;" Ser. No. 10/739,895, filed on Dec. 18, 2003, entitled "Method of Operating a Beverage Container Filling Plant with a Labeling Machine for Labeling Beverage Containers Such as Bottles and Cans, and a Beverage Container Filling Plant with a Labeling Machine for Labeling Beverage Containers Such as Bottles and Cans;" Ser. No. 10/865,240, filed on Jun. 10, 2004, Entitled "A Beverage Bottling Plant for Filling Bottles with a Liquid Beverage Filling Material, a Beverage Container Filling Machine, and a Beverage Container Closing Machine;" Ser. No. 10/883,591, filed on Jul. 1, 2004, entitled "A Beverage Bottling Plant for Filling Bottles with a Liquid Beverage Filling Material Having a Container Filling Plant Container Information Adding Station, Such As, a Labeling Station, Configured to Add Information to Containers, Such As, Bottles and Cans, and Modules for Labeling Stations and a Bottling Plant Having a Mobile Module Carrier;" Ser. No. 10/930,678, filed on Aug. 31, 2004, entitled "A Beverage Bottling Plant for Filling Bottles with a Liquid Beverage Filling Material, a Container Filling Plant Container Filling Machine, and a Filter Apparatus for Filtering a Liquid Beverage;" Ser. No. 10/931,817, filed on Sep. 1, 2004, entitled "A Beverage Bottling Plant for Filling Bottles with a Liquid Beverage Filling Material, Having an Apparatus for Exchanging Operating Units Disposed at Rotating Container Handling Machines;" Ser. No. 10/954,012, filed on Sep. 29, 2004; Ser. Nos. 10/952,706; 10/962,183, filed on Oct. 8, 2004; Ser. No. 10/967,016, filed on Oct. 15, 2004; Ser. No. 10/982,706, filed on Nov. 5, 2004; Ser. Nos. 10/982,694; 10/982,710; Ser. No. 10/984,677, filed on Nov. 9, 2004; Ser. No. 10/985,640, filed on Nov. 10, 2004; Ser. No. 11/004,663, filed on Dec. 3, 2004; Ser. No. 11/009,551, filed on Dec. 10, 2004; Ser. No. 11/012,859, filed on Dec. 15, 2004; Ser. No. 11/014,673, filed on Dec. 16, 2004; Ser. No. 11/016,364, filed on Dec. 17, 2004; and Ser. No. 11/016,363.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

Some examples of bottling systems, which may be used or adapted for use in at least one possible embodiment of the present may be found in the following U.S. Patents assigned to the Assignee herein, namely: U.S. Pat. Nos. 4,911,285; 4,944,830; 4,950,350; 4,976,803; 4,981,547; 5,004,518; 5,017,261; 5,062,917; 5,062,918; 5,075,123; 5,078,826; 5,087,317; 5,110,402; 5,129,984; 5,167,755; 5,174,851; 5,185,053; 5,217,538; 5,227,005; 5,413,153; 5,558,138; 5,634,500; 5,713,403; 6,276,113; 6,213,169; 6,189,578; 6,192,946; 6,374,575; 6,365,054; 6,619,016; 6,474,368; 6,494,238; 6,470,922; and 6,463,964.

The appended drawings in their entirety, including all dimensions, proportions and/or shapes in at least one embodiment of the invention, are accurate and are hereby included by reference into this specification.

Some examples of apparatus and methods of sterilizing or cleaning containers that may possibly be utilized or possibly adapted for use in at least one possible embodiment of the present application may possibly be found in the following U.S. Pat. No. 5,092,356 issued to Grot on Mar. 3, 1992; U.S. Pat. No. 5,320,144 issued to Ahlers on Jun. 14, 1994; U.S. Pat. No. 5,533,552 issued to Ahlers on Jul. 9, 1996; U.S. Pat. No. 5,558,135 issued to Kronseder et al. on Sep. 24, 1996; and U.S. Pat. No. 5,896,899 issued to Schlitz on Apr. 27, 1999.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Some examples of control systems which measure operating parameters and learn therefrom that may possibly be utilized or possibly adapted for use in at least one possible embodiment of the present application may possibly be found in the following U.S. patents: U.S. Pat. No. 4,655,188 issued to Tomisawa et al. on Apr. 7, 1987; U.S. Pat. No. 5,191,272 issued to Torii et al. on Mar. 2, 1993; U.S. Pat. No. 5,223,820, issued to Sutterlin et al. on Jun. 29, 1993; and U.S. Pat. No. 5,770,934 issued to Theile on Jun. 23, 1998.

All, or substantially all, of the components and methods of the various embodiments may be used with at least one embodiment or all of the embodiments, if more than one embodiment is described herein.

Some examples of sterilizing or cleaning agents and concentrations thereof that may possibly be utilized or possibly adapted for use in at least one possible embodiment of the present application may possibly be found in the following U.S. Pat. No. 6,039,922 issued to Swank et al. on Mar. 21, 2000; U.S. Pat. No. 6,244,275 issued to Ziegler et al. on Jun. 12, 2001; U.S. Pat. No. 6,406,666 issued to Cicla et al. on Jun. 18, 2002; and U.S. Pat. No. 6,612,149 issued to Wang et al. on Sep. 2, 2003.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

Some examples of nozzle structures that may possibly be utilized or possibly adapted for use in at least one possible embodiment of the present application may possibly be found in the following U.S. Pat. No. 6,042,026 issued to Buehler, II on Mar. 28, 2000; U.S. Pat. No. 6,394,366 issued to Adams on May 28, 2002; U.S. Pat. No. 6,402,062 issued to Bendig et al. on Jun. 11, 2002; U.S. Pat. No. 6,616,072 issued to Harata et al. on Sep. 9, 2003; U.S. Pat. No. 6,666,386 issued to Huang on Dec. 23, 2003; and U.S. Pat. No. 6,681,498 issued to Steffan on Jan. 27, 2004.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the German Office Action dated Oct. 13, 2006, and/or cited elsewhere are hereby incorporated by reference as if set forth in their entirety herein as follows: German Patent No. 199 49 692 A1, German Patent No. 30 47 087 A1, German Patent No. 90 12 065 U1.

The corresponding foreign and international patent publication applications, namely, Federal Republic of Germany Patent Application No. 10 2006 007 944.2, filed on Feb. 21, 2006, having inventors Volker TILL and Daryoush SANGI, and DE-OS 10 2006 007 944.2 and DE-PS 10 2006 007 944.2, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C. F. R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of operating a beverage filling plant for filling containers with liquid beverage material, each of which containers comprises: a mouth portion, a main body portion, and a curved, hollow handle portion comprising an upper handle portion connected to an upper body portion of said main body portion adjacent said mouth portion, and a lower handle portion connected to a lower body portion of said main body portion adjacent the bottom of said container; said method comprising the steps of:

moving containers to a container sterilizing machine;

sterilizing the interior surfaces of said containers by dispensing aerosol sterilizing medium comprising hydrogen peroxide into said containers;

moving containers from said container sterilizing machine to a container filling machine;

moving containers with a first star wheel structure into container carriers disposed on the periphery of a rotatable rotor of said container filling machine;

conducting liquid beverage material from at least one liquid reservoir to a plurality of filling elements disposed on the periphery of said rotor;

activating said filling elements and filling containers with liquid beverage material;

moving filled containers with a second star wheel structure out of said container filling machine;
moving containers to a container closing machine;
moving containers with a third star wheel structure into container carriers disposed on the periphery of a rotatable rotor of said container closing machine;
conducting container closures from a supply of container closures to a plurality of closing elements disposed on the periphery of said rotor of said container closing machine;
activating said closing elements and closing filled containers;
moving filled, closed containers with a fourth star wheel structure out of said container closing machine; and
said step of sterilizing comprising:
  moving a substantially tube-shaped nozzle structure of said container sterilizing machine into a container through its mouth portion, which nozzle structure has a central longitudinal axis and comprises: a central conduit disposed therein, a first nozzle opening connected to said central conduit, and a second nozzle opening connected to said central conduit;
  positioning said nozzle structure and said second nozzle opening in a predetermined position, in which said second nozzle opening faces toward said upper handle portion, by positioning a bracket portion of said nozzle structure in a predetermined position, which bracket portion is disposed to project substantially radially with respect to said central longitudinal axis of said nozzle structure;
  supplying aerosol sterilizing medium into said nozzle conduit, which said nozzle conduit has a larger cross-sectional diameter than the cross-sectional diameter of any one of said nozzle openings;
  sterilizing the interior surfaces of said main body portion of said container by shooting a first jet of sterilizing medium downwardly through said first nozzle opening and into said main body portion of said container, which said first nozzle opening is disposed substantially coaxially to said central longitudinal axis of said nozzle structure;
  sterilizing the interior surfaces of said handle portion by shooting a second jet of sterilizing medium downwardly through said second nozzle opening and into said upper handle portion at a first, acute angle with respect to a plane extending perpendicular to said central longitudinal axis of said nozzle structure in a direction substantially along the slope of curvature of said upper handle portion, which said second nozzle opening is disposed in a downwardly sloping direction at said first, acute angle with respect to the plane extending perpendicular to said central longitudinal axis of said nozzle structure; and
  conducting sterilizing medium from said second nozzle opening through said upper handle portion, through said lower handle portion, then out of said lower handle portion and into said main body portion of said container.

2. The method according to claim 1, wherein:
said nozzle structure comprises a third nozzle opening disposed adjacent said second nozzle opening;
said step of positioning said nozzle structure and said second nozzle opening in a predetermined position comprises positioning said third nozzle opening in a predetermined position, in which said third nozzle opening faces toward said upper handle portion; and
said step of sterilizing the interior surfaces of said handle portion further comprises shooting a third jet of sterilizing medium through said third nozzle opening and into said upper handle portion at a second angle with respect to the plane extending perpendicular to said central longitudinal axis of said nozzle structure, which second angle is different from said first, acute angle, and which said third nozzle opening is disposed in a direction at said second angle with respect to the plane extending perpendicular to said central longitudinal axis of said nozzle structure.

3. The method according to claim 2, wherein said treatment medium essentially comprises an aerosol mixture of sterile air and hydrogen peroxide.

4. The method according to claim 3, wherein said second angle is less than said first, acute angle.

5. The method according to claim 3, wherein said second angle is zero with respect to the plane extending perpendicular to said central longitudinal axis of said nozzle structure.

6. A method of operating a beverage filling plant for filling containers with liquid beverage material, each of which containers comprises a main body portion and a contoured mouth portion comprising a hollow, annular projection comprising a concave interior surface, said method comprising the steps of:
moving containers to a container sterilizing machine;
sterilizing the interior surfaces of said containers by dispensing aerosol sterilizing medium comprising hydrogen peroxide into said containers;
moving containers from said container sterilizing machine to a container filling machine;
moving containers with a first star wheel structure into container carriers disposed on the periphery of a rotatable rotor of said container filling machine;
conducting liquid beverage material from at least one liquid reservoir to a plurality of filling elements disposed on the periphery of said rotor;
activating said filling elements and filling containers with liquid beverage material;
moving filled containers with a second star wheel structure out of said container filling machine;
moving containers to a container closing machine;
moving containers with a third star wheel structure into container carriers disposed on the periphery of a rotatable rotor of said container closing machine;
conducting container closures from a supply of container closures to a plurality of closing elements disposed on the periphery of said rotor of said container closing machine;
activating said closing elements and closing filled containers;
moving filled, closed containers with a fourth star wheel structure out of said container closing machine; and
said step of sterilizing comprising:
  moving a substantially tube-shaped nozzle structure of said container sterilizing machine into a container through its mouth portion, which nozzle structure has a central longitudinal axis and comprises: a central conduit disposed therein, a first nozzle opening connected to said central conduit, a first plurality of nozzle openings connected to said central conduit and disposed a first distance from said first nozzle measured along the central longitudinal axis, a second plurality of nozzle openings connected to said central conduit and disposed between said first plurality of nozzle openings and said first nozzle measured along the central longitudinal axis, and a third plurality of nozzle openings connected to said central conduit and disposed between said second plurality of nozzle openings and said first nozzle measured along the central longitudinal axis;

positioning said nozzle structure and said pluralities of nozzle openings in a predetermined position, in which said pluralities of nozzle openings face toward said concave interior surface of said annular projection;

supplying aerosol sterilizing medium into said nozzle conduit, which said nozzle conduit has a larger cross-sectional diameter than the cross-sectional diameter of any one of said nozzle openings;

sterilizing the interior surfaces of said main body portion of said container by shooting a jet of sterilizing medium through said first nozzle opening and into said main body portion of said container, which said first nozzle opening is disposed substantially coaxially to said central longitudinal axis of said nozzle structure; and sterilizing the concave interior surfaces of said annular projection by:

shooting a jet of sterilizing medium through each of said first plurality of nozzle openings at an acute angle with respect to a plane extending perpendicular to said central longitudinal axis of said nozzle structure in a direction toward an upper portion of the concave interior surfaces of said annular projection, each of which said first plurality of nozzle openings is disposed at an acute angle with respect to the plane extending perpendicular to said central longitudinal axis of said nozzle structure; and substantially simultaneously shooting a jet of sterilizing medium through each of said second plurality of nozzle openings substantially in a plane extending perpendicular to said central longitudinal axis of said nozzle structure in a direction toward a middle portion of the concave interior surfaces of said annular projection, each of which said second plurality of nozzle openings is disposed to lie substantially within the plane extending perpendicular to said central longitudinal axis of said nozzle structure; and substantially simultaneously shooting a jet of sterilizing medium through each of said third plurality of nozzle openings at an acute angle with respect to a plane extending perpendicular to said central longitudinal axis of said nozzle structure in a direction toward a lower portion of the concave interior surfaces of said annular projection, each of which said third plurality of nozzle openings is disposed at an acute angle with respect to the plane extending perpendicular to said central longitudinal axis of said nozzle structure.

7. The method according to claim 6, wherein said treatment medium essentially comprises an aerosol mixture of sterile air and hydrogen peroxide.

8. A method of operating a beverage filling plant for filling containers with liquid beverage material, each of which containers comprises: a mouth portion, a main body portion, and a curved, hollow handle portion comprising an upper handle portion connected to an upper portion of said container, and a lower handle portion connected to a portion of said container lower than said upper handle portion; said method comprising the steps of:

moving containers to a container sterilizing machine;

sterilizing the interior surfaces of said containers by dispensing sterilizing medium into said containers;

moving containers out of said container sterilizing machine and into a container filling machine;

filling containers with liquid beverage material;

moving filled containers out of said container filling machine and into a container closing machine;

closing filled containers;

said step of sterilizing comprising:

moving a nozzle structure of said container sterilizing machine into a container through its mouth portion, which nozzle structure has a longitudinal axis and comprises: a first nozzle opening and a second nozzle opening;

positioning said nozzle structure and said second nozzle opening in a predetermined position, in which said second nozzle opening faces toward said upper handle portion, by positioning an alignment structure of said nozzle structure in a predetermined position;

supplying sterilizing medium into said nozzle structure;

sterilizing the interior surfaces of said main body portion of said container by dispensing sterilizing medium through said first nozzle opening and into said main body portion of said container;

sterilizing the interior surfaces of said handle portion by dispensing sterilizing medium through said second nozzle opening and into said upper handle portion at a non-zero angle with respect to a plane extending perpendicular to said longitudinal axis of said nozzle structure; and conducting sterilizing medium from said second nozzle opening through said upper handle portion, through said lower handle portion, then out of said lower handle portion and into said main body portion of said container.

9. The method according to claim 8, wherein:

said nozzle structure comprises a third nozzle opening disposed adjacent said second nozzle opening;

said step of positioning said nozzle structure and said second nozzle opening in a predetermined position comprises positioning said third nozzle opening in a predetermined position, in which said third nozzle opening faces toward said upper handle portion; and said step of sterilizing the interior surfaces of said handle portion further comprises dispensing sterilizing medium through said third nozzle opening and into said upper handle portion at a second angle with respect to the plane extending perpendicular to said central longitudinal axis of said nozzle structure, which second angle is different from said non-zero angle.

10. The method according to claim 9, wherein said step of sterilizing the interior surfaces of said handle portion by dispensing sterilizing medium through said second nozzle opening comprises shooting a jet of sterilizing medium downwardly through said second nozzle opening and into said upper handle portion at a first, acute angle with respect to the plane extending perpendicular to said longitudinal axis of said nozzle structure in a direction substantially along the slope of curvature of said upper handle portion, which said second nozzle opening is disposed in a downwardly sloping direction at said first, acute angle with respect to the plane extending perpendicular to said central longitudinal axis of said nozzle structure.

11. The method according to claim 10, wherein said alignment structure comprises a bracket portion, which bracket portion is disposed to project substantially radially with respect to said longitudinal axis of said nozzle structure.

12. The method according to claim 11, wherein:
said nozzle structure comprises a nozzle conduit connected to each of said nozzle openings to supply treatment medium to said nozzle openings; and
the cross-sectional diameter of any one of said nozzle openings is less than the cross-sectional diameter of said nozzle conduit to constrict flow of treatment medium through said nozzle openings and increase pressure to a level sufficient to dispense a quantity of treatment medium sufficient to sterilize the interior surfaces of said containers.

13. The method according to claim 12, wherein said first nozzle opening is disposed substantially coaxially to said longitudinal axis of said nozzle structure.

14. The method according to claim 13, wherein said treatment medium essentially comprises an aerosol mixture of sterile air and hydrogen peroxide.

15. The method according to claim 14, wherein said nozzle structure comprises a tube-shaped nozzle structure.

16. The method according to claim 15, wherein said second angle is less than said first, acute angle.

17. The method according to claim 16, wherein said second angle is zero with respect to the plane extending perpendicular to said central longitudinal axis of said nozzle structure.

18. The method according to claim 17, wherein said treatment medium consists of an aerosol mixture of sterile air and hydrogen peroxide.

19. The method according to claim 18, wherein said filling machine comprises a rotary filling machine, and said closing machine comprises a rotary closing machine.

* * * * *